July 29, 1969 W. FLEMER III Plant Pat. 2,913
CRAB APPLE TREE
Filed Oct. 5, 1967
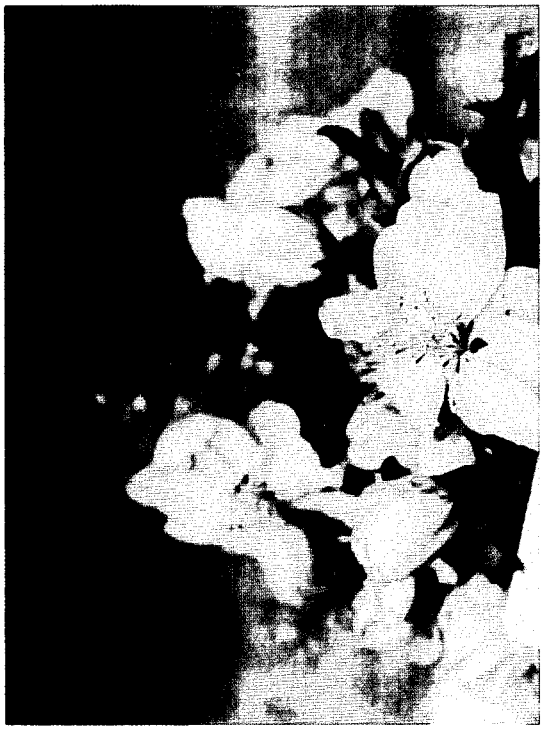
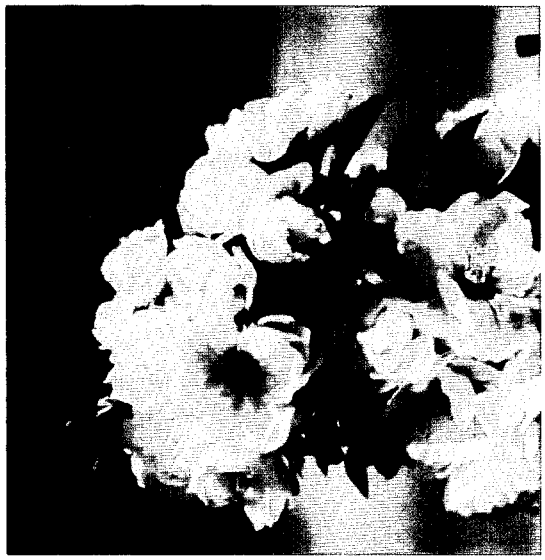
Inventor.
William Flemer, III
By: Robb & Robb
Attorneys.

United States Patent Office

Plant Pat. 2,913
Patented July 29, 1969

2,913

CRAB APPLE TREE

William Flemer III, Princeton, N.J., assignor to Treesearch, Kingston, N.J., a partnership

Filed Oct. 5, 1967, Ser. No. 673,238
Int. Cl. A01h *5/08*
U.S. Cl. Plt.—34 1 Claim

The present invention relates to a new and distinct variety of flowering crab apple tree which was originated by me by crossing the crab apple variety known as "Katherine" (unpatented) with the crab apple variety known as "Almey" (unpatented).

As the result of this breeding, I have produced a new and improved variety of flowering crab apple tree, botanically known as a Malus hybrid, which is distinguished from its parents, as well as from all other varieties of which I am aware, as evidenced by the following unique combination of characteristics which are outstanding therein:

(1) An exceptional vigorous habit of growth as compared with other double-flowered varieties of Asiatic origin;

(2) A non-defoliating habit under unfavorable weather conditions attributable to relatively high summer temperatures and humidity which prevail in New Jersey;

(3) Large, double flowers which are borne in large clusters so densely as to hide the branches;

(4) A pure white flower color when the flowers fully open;

(5) A high resistance to fire blight as compared with other varieties commonly grown in New Jersey; and (6) Sparse production of fruit, with the fruit being free from disfiguration by apple scab disease.

Asexual reproduction of my new variety by bud grafting, as performed by me in Plainsboro Township, N.J., shows that the foregoing characteristics and distinctions come true to form and are established and transmitted through succeeding propagations.

The accompanying drawing shows a typical specimen of the top portion of a young tree of my new variety with fully open mature white flowers borne thereon, and also separately shows typical pink buds and immature flowers as depicted on a somewhat enlarged scale, all as depicted in color as nearly true as it is reasonably possible to make the same in a color illustration of this character.

The following is a detailed description of my new variety, with color terminology in accordance with the Munsell Color Chart, except where general color terms of ordinary dictionary significance are obvious:

Parentage: Seedling.
- *Seed parent.*—M. "Katherine."
- *Pollen parent.*—M. "Almey."

Locality where grown and observed: Plainsboro Township, N.J.

Tree: Medium size; upright; dense; medium height; hardy.
- *Trunk.*—Stocky; smooth.
- *Branches.*—Stocky; smooth. Lenticels—moderately abundant in number.
- *Color.*—Moderate Reddish-Brown, Hue 10R 3/4.

Foliage:
- *Leaves.*—Abundant. Size: length (not including petiole)—about 10 cm.; width—about 5 cm. Shape—ovate; pointed. Thickness—medium. Color—Dark Yellowish-Green, Hue 2.5G 3/3. Margin—serrate. Petiole—medium length (about 3 cm. long). Glands—none. Stipules—about 2 cm. long.

Flower buds:
- *Hardiness.*—Very hardy.
- *Size.*—Large. Length—about 2 cm. Width—about 1.5 cm.
- *Clusters.*—7 or 8 per cluster.
- *Shape.*—Ovate; pointed.
- *Color.*—From Deep Pink, Hue 2.5R 6/11 to near Moderate Red, Hue 2.5R 4/10.

Flowers:
- *Blooming season.*—First bloom—about May 5 in central New Jersey. Full bloom—about May 12 in central New Jersey.
- *Quantity.*—Very abundant.
- *Size.*—Very large (from 6.5 to 7.5 cm. in diameter).
- *Color.*—Pure white when fully open.
- *Petalage.*—Double. Number of petals—13 or 14 petals. Shape—spatulate; rounded. Size of petals: length—about 3 cm.; width—about 2 cm.

Fruit:
- *Borne.*—September-October.
- *Abundance.*—Sparse.
- *Shape.*—Flattened; globular.
- *Size.*—Length—about 1 cm. Width—about 1.2 cm.
- *Color.*—Yellow, Hue 2.5GY 9/8.

I claim:

1. A new and distinct variety of flowering crab apple tree, substantially as herein shown and described, characterized particularly as to novelty by the unique combination of an exceptional vigorous habit of growth as compared with other double-flowered varieties of Asiatic origin, a non-defoliating habit under unfavorable weather conditions prevalent in New Jersey, large double flowers which are borne in large clusters so densely as to hide the branches, a pure white flower color when the flowers fully open and are mature, a high resistance to fire blight as compared with other varieties commonly grown in New Jersey, and sparse production of fruit, with the fruit being free from disfiguration by apple scab disease.

No references cited.

ROBERT E. BAGWILL, Primary Examiner